US009429845B2

(12) United States Patent
Ohtake et al.

(10) Patent No.: US 9,429,845 B2
(45) Date of Patent: Aug. 30, 2016

(54) METHOD OF PATTERNING SELF-ORGANIZING MATERIAL, PATTERNED SUBSTRATE OF SELF-ORGANIZING MATERIAL AND METHOD OF PRODUCING THE SAME, AND PHOTOMASK USING PATTERNED SUBSTRATE OF SELF-ORGANIZING MATERIAL

(71) Applicants: Toshihito Ohtake, Mino (JP); Ken-ichiro Nakamatsu, Aioi (JP); Shinji Matsui, Himeji (JP); Hitoshi Tabata, Suita (JP); Tomoji Kawai, Mino (JP)

(72) Inventors: Toshihito Ohtake, Mino (JP); Ken-ichiro Nakamatsu, Aioi (JP); Shinji Matsui, Himeji (JP); Hitoshi Tabata, Suita (JP); Tomoji Kawai, Mino (JP)

(73) Assignee: Japan Science and Technology Agency, Saitama (JP)

( * ) Notice: Subject to any disclaimer, the term of this patent is extended or adjusted under 35 U.S.C. 154(b) by 439 days.

(21) Appl. No.: 13/898,105

(22) Filed: May 20, 2013

(65) Prior Publication Data

US 2013/0330674 A1 Dec. 12, 2013

Related U.S. Application Data

(62) Division of application No. 11/663,826, filed as application No. PCT/JP2005/017930 on Sep. 29, 2005, now abandoned.

(30) Foreign Application Priority Data

Sep. 30, 2004 (JP) .................................. 2004-287549

(51) Int. Cl.
*B82Y 40/00* (2011.01)
*C12Q 1/68* (2006.01)

(Continued)

(52) U.S. Cl.
CPC ................. *G03F 7/20* (2013.01); *B82Y 10/00* (2013.01); *B82Y 40/00* (2013.01); *G03F 7/0002* (2013.01);

(Continued)

(58) Field of Classification Search
None
See application file for complete search history.

(56) References Cited

U.S. PATENT DOCUMENTS 5,466,348 A 11/1995 Holm-Kennedy
5,605,662 A 2/1997 Heller et al.

(Continued)

FOREIGN PATENT DOCUMENTS

WO WO 2004/055920 7/2004

OTHER PUBLICATIONS

Falconnet et al, Nano Letters, vol. 4, pp. 1909-1914, published on the Web Sep. 21, 2004.*

(Continued)

*Primary Examiner* — Robert T Crow
(74) *Attorney, Agent, or Firm* — Harness, Dickey & Pierce, PLC

(57) ABSTRACT

A method for performing micro fabrication includes using, as a photomask, a self-organizing material-patterned substrate which is soluble in an organic solvent. A method for emitting light includes emitting the light in a pattern of a nucleic acid which is a self-organizing material immobilized on a self-organizing material-patterned substrate. An immobilization layer containing a binding material capable of binding to a self-organizing material is formed on a substrate. Then this immobilization layer is patterned by transferring a protrusion and recess pattern formed in a mold thereto by the imprint process. The self-organizing material is supplied onto the side having the protrusion and recess pattern of the immobilization layer transferred thereto. Thus, the self-organizing material is immobilized according to the protrusion and recess pattern of the immobilization layer owning to the self-organizing ability of the material per se and the binding ability of the binding material contained in the immobilization layer.

3 Claims, 6 Drawing Sheets

(51) Int. Cl.
  G03F 7/20      (2006.01)
  B82Y 10/00     (2011.01)
  G03F 7/00      (2006.01)
  H01L 51/00     (2006.01)
  G01N 21/552    (2014.01)

(52) U.S. Cl.
  CPC ......... *H01L 51/0022* (2013.01); *G01N 21/553* (2013.01); *G01N 21/554* (2013.01); *H01L 2251/105* (2013.01); *Y10T 428/24802* (2015.01)

(56) References Cited

U.S. PATENT DOCUMENTS

| | | |
|---|---|---|
| 6,586,193 B2 | 7/2003 | Yguerabide et al. |
| 6,652,808 B1 | 11/2003 | Heller et al. |
| 6,653,653 B2 | 11/2003 | Brousseau, III |
| 2002/0110932 A1 | 8/2002 | Wagner et al. |
| 2003/0186274 A1 | 10/2003 | Limoges et al. |
| 2004/0043379 A1 | 3/2004 | Hashimoto et al. |
| 2005/0272885 A1 | 12/2005 | Mirkin et al. |

OTHER PUBLICATIONS

Zhang et al., "The Immobilization of DNA on microstructured patterns fabricated by maskless lithography," vol. 97, pp. 243-248, (Nov. 7, 2003).
A. Pépin. "Nanoimprint lithography for the fabrication of DNA electrophoresis chips". Microelectronic Engineering vol. 61-62, pp. 927-932, Jul. 2002.
T. Ohtaka et al. "30p-ZQ-1 Self-Organizing DNA Nano-pattorning by using Nanoimprint" Institute of Tech. vol. 51th, No. 3, p. 1503, Mar. 28, 2004.
Fumihiko Yamada. "30p-ZQ-2 DNO-templated assembly of gold nanoparticles". Osaka University. vol. 51th, No. 3, p. 1503, Mar. 28, 2004.
Okaoru Ojima et al. "2p-ZT-17 DNA One dimensional ordering of Au particles using a DNA template". Osaka University. vol. 65th, No. 3, p. 1205, Sep. 1, 2004.
"Radiation Application Technology Database, Data No. 018015." Home Page of Radiation Application Development Association.
Jun Taniguchi et al., "Recent Trend of Nanoimprint Technique." Journal of the Japan Society for Abrasive Technology, vol. 46, No. 6, pp. 282-285, 2002.
T. Ohtake et al., "30p-Zq-1 Self-Organizing DNA Nano-patterning by using Nanoimprint." Institute of Tech. vol. $51^{st}$, No. 3, p. 1503, issued on Mar. 28, 2004, announced on Mar. 30, 2004.
L. R. Harriott et al., "Preliminary results from a prototype projection electron-beam stepper-scattering with angular limitation projection electron beam lithography proof-of-concept system." J. Vac. Sci. Technol. B14 (6), pp. 3825-3828, 1996.
T. Yoshimura et al., "Nano edge roughness in polymer resist patterns." Appl. Phys. Lett. 63 (6), pp. 764-766, Aug. 9, 1993.
J. Yamamoto et al., "Nanometer Electron Beam Lithography with Azide-Phenolic Resin Resist Systems." Jpn. J. Appl. Phys. vol. 35, pp. 6511-6516, 1996.
G. Gross et al., "Ion projection lithography: Status of the MEDEA project and United States/European cooperation." J. Vac. Sci. Technol. B16(6), pp. 3150-3153, 1998.
M. Ueda et al., "Atomic Force Microscopy Observation of Deoxyribonucleic Acid Stretched and Anchored onto Aluminum Electrodes." Jpn. J. Appl. Phys. vol. 38, pp. 2118-2119, 1999.
R. Singhvi et al., "Engineering Cell Shape and Function." Science, 264 (5159), pp. 696-698, Apr. 29, 1994.
A. Kumar et al., "Patterning Self-Assembled Monolayer: Applications in Materials Science." Langmuir, (10), pp. 1498-1511, 1994.
Xu et al., "The contribution of poly-L-lysine, epidermal growth factor and streptavidin to EGF/PLL/DNA polyplex formation." Gene Therapy 5, pp. 1235-1243, 1998.
K. Keren et al., "Patterned DNA Metallization by Sequence-Specific Localization of a Reducing Agent." Nano Lett. vol. 4, No. 2, pp. 323-326, 2004.
J. Richter et al., "Construction of highly conductive nanowires on a DNA template." Appl. Phys. Lett. vol. 78, No. 4, pp. 536-538, Jan. 22, 2001.
E. Braun et al., "DNA-templated assembly and electrode attachment of a conducting silver wire." Nature vol. 391, pp. 775-778, Feb. 19, 1998.
R. Seidel et al., "Scanning force microscopy of DNA metallization." Surf. Interface Anal. (33), pp. 151-154, 2002.
S.O. Kelley et al., "Orienting DNA Helices on Gold Using Applied Electric Fields." Langmuir, vol. 14, No. 24, pp. 6781-6784, Nov. 24, 1998.
European Search Report dated Nov. 23, 2010 in European Patent Application No. 05788374.6.
U.S. Office Action issued in U.S. Appl. No. 11/663,826, dated Aug. 17, 2012.
U.S. Office Action issued in U.S. Appl. No. 11/663,826, dated Feb. 21, 2013.

\* cited by examiner

MOLD (SiO$_2$)

DNA PATTERN

MOLD (SiO$_2$)

DNA PATTERN

METHOD OF PATTERNING SELF-ORGANIZING MATERIAL, PATTERNED SUBSTRATE OF SELF-ORGANIZING MATERIAL AND METHOD OF PRODUCING THE SAME, AND PHOTOMASK USING PATTERNED SUBSTRATE OF SELF-ORGANIZING MATERIAL

TECHNICAL FIELD

The present invention relates to a patterning method for immobilizing a self-organizing material in a desired pattern on a substrate by utilizing an imprinting process, the self-organizing material (such as nucleic acid or the like) having a self-organizing function, a self-organizing material-patterned substrate patterned with the self-organizing material in a desired pattern, and a method of producing the same, and a photomask made of the self-organizing material-patterned substrate.

BACKGROUND ART

In industrial materials and the like such as semiconductors typically, photolithography is generally used to perform micro fabrication. The photolithography is a technique for transferring or reprinting by radiating light, through a photomask, a photoresist applied on a silicon substrate thereby to perform reduced projection of a pattern of the photomask on the photoresist (see Non-Patent Citation 1). The photolithography makes it possible to produce wiring with fine diameters that had been impossible to make by conventional methods for processing parts in micro sizes.

For finer wirings, techniques to replace the techniques using light have been developed recently: a lithography techniques using an X ray (non-Patent citation 1), lithography techniques in which drawing is carried out by an electron beam directly (Non-Patent Citation 2, 3, and 4), lithography technique using an ion beam (non-Patent Citation 5), and the like techniques.

As they become capable of processing finer, these lithography techniques requires an exponential increase in an initial cost for an exposing apparatus itself. Moreover, some of the lithography techniques using masks face an increase in a cost of masks that make it possible to attain resolutions as much as the light wavelength to use.

In view of this, imprinting process has been remarked as a processing technique that attains a resolution of the order of 10 nm with low cost (Non-Patent Citation 6). The imprinting process is a processing technique for transferring a fine pattern of a mold on a resist by pressing the mold on the resist. The imprinting process makes it possible to perform microfabrication easily with low cost. With the imprinting process, a nano-scale structure can be formed quite easily.

Moreover, inventors of the present invention has already proposed a patterning method in which a poly-L-lysine layer is formed as a DNA immobilization layer on a glass substrate, and a DNA layer is immobilized on the DNA immobilization layer, and the DNA layer is patterned by imprinting process (Non-Patent Citation 7).

As an art in which a nucleic acid (typically DNA) is provided on a substrate, there is an attempt in for extending DNA straightly on a glass substrate by adding DNA in a gap between a pair of aluminum electrodes provided on the glass substrate and applying static electricity thereon (Non-Patent Citation 8). This technique, however, cannot form a pattern in a desired shape.

Furthermore, a micro contact printing method is also known (Non-Patent Citations 9 and 10). In the micro contact printing method, a stamp is prepared by transferring a micro-meter-sized pattern of a structure onto a rubber-like plastic, and molecules such as thiol or aminosilane, which forms a self-organizing film, are applied on surfaces of protrusions of the stamp. Then, the stamp is pressed against the substrate so as to form a patterned molecular film on the substrate by utilizing a chemical reaction between the molecules and the surface of the substrate. For example, in case where a molecular is formed using aminosilane, DNA is adsorbed to the molecular film if the DNA solution is applied onto the molecular film.

[Non-Patent Citation 1]
Radiation Application Development Association: Radiation Application Research Database; data number 018015
[Non-Patent Citation 2]
L. R. Harriot., S. D. Berger., C. Biddick., M. I. Blakey., S. W. Bowler., K. Brady., R. M. Camarda., W. F. Connelly., A. Crorken., J. Custy., R. Dimarco., R. C. Farrow., J. A. Felker., L. Fetter., R. Freeman., L. Hopkins., H. A. Huggins., C. S. Knurek., J. S. Kraus., J. A. Liddle., M. Mkrtychan., A. E. Novembre., M. L. Peabody., R. G. Tarascon., H. H. Wade., W. K. Waskiewicz., G. P. Watson., K. S. Werder and D. Windt., J. Vac. Sci. Technol. B14(6), 3825-3828, 1996
[Non-Patent Citation 3]
T. Yoshimura., H. Shiraishi., J. Yamamoto., and S. Okazaki., Appl. Phys. Lett. (63), 764-766, 1993
[Non-Patent Citation 4]
J. Yamamoto., S. Uchino., T. Hattori., T. Yoshimura., and F. Murai., Jpn. J. Appl. Phys. (35), 6511-6516, 1996
[Non-Patent Citation 5]
G. Gross., and R. Kaesmaier., J. Vac. Sci. Technol. B16(6), 1998
[Non-Patent Citation 6]
Jun TANIGUCHI, Iwao MIYAMOTO, Masanori FURUMURO, and Shinji MATSUI, Journal of the Japan Society for Abrasive Technology, vol. 46, No. 6, 282-285, 2002
[Non-Patent Citation 7]
Toshihito OTAKE, Kenichiro NAKAMATSU, Shinji MATSUI, Hitoshi TABATA, and Tomoji KAAI, The spring meeting of Jpn. Soci. of Appl. Phys. in 2004 (Mar. 30, 2004), Digest of the spring meeting in 2004, No, 3, p. 1503
[Non-Patent Citation 8]
M. Ueda., H. Iwasaki., O. Kurosawa., and M. Washizu., Jpn. J. Appl. Phys. (38), 2118-2119, 1999
[Non-Patent Citation 9]
R. Singhvi; A. Kumar; G. P. Lopez; G. N. Stephanopoulos; D. I. C. Wang; G. M. Whitesides; D. E. Ingber. Science, 1994, 264 (5159), 696-698.
[Non-Patent Citation 10]
A. Kumar., H. A. Biebuyck., and G. Whitesides., Langmuir, (10), 1498-1511, 1994

As described above, various microfabrication techniques have been developed so far. However, these conventional techniques are not capable of patterning a biomaterial, namely, a nucleic acid (DNA or RNA) in a desired shape (desired pattern) on a substrate.

To begin with, the conventional techniques described in Non-Patent Citations 1 to 5 are discussed. The nucleic acid is a biomaterial and thus is not tolerant against radiation of x ray, electron beam, ion beam and the like, and may be denatured by an organic solvent. Therefore, the structure and function of the nucleic acid cannot be maintained in the conventional techniques described in Non-Patent Citations 1 to 5 in which x ray, electron beam, ion beam or the like is irradiated and an organic solvent is used.

On the other hand, the structure and function of the nucleic acid can be maintained by the methods described in Non-Patent Citations 6 to 9, which utilize DNA that is a biomaterial.

However, the method described in Non-Patent Citation 8 is merely capable of extending DNA on the substrate straightly, and cannot immobilize DNA in a desired pattern on the substrate.

In the methods described in Non-Patent Citations 9 and 10, the transfer of the molecules is carried out by pressuring the stamp onto the substrate in contact. Thus, it is not desirable for biomolecule such as DNA to employ such a process in which a load is applied on the molecules. Moreover, combinations of kinds of substrates and molecular films are limited because the molecular film is formed by the chemical reaction between the surface of the substrate and molecules. This gives a limitation to materials of the substrate on which the DNA film is formable.

Meanwhile, the method described in Non-Patent Citation 7 and proposed by the inventors of the present invention previously can perform the patterning in a desired pattern with DNA. However, the method described in Non-Patent Citation 7 uses a general imprinting process for imprinting DNA. Such as imprinting would possibly damage the structure and function of DNA by pressure, heat or light in imprinting.

The present invention was accomplished in view of the aforementioned problem. An object of the present invention is to provide a patterning method in which a self-organizing material such as a nucleic acid or the like having a self-organizing ability is immobilized in a predetermined pattern on a substrate by utilizing imprinting process, and a self-organizing material-patterned substrate in which the self-organizing material is patterned in a predetermined pattern, and a method of producing the self-organizing material-patterned substrate, and a photomask including the self-organizing material-patterned substrate.

DISCLOSURE OF INVENTION

In order to attain the object, a method according to the present invention is a method of patterning a self-organizing material, including: forming, on a substrate, an immobilization layer containing the binding material having an ability of binding (binding ability) with the self-organizing material having a self-organizing ability; patterning the immobilization layer by transferring a protrusion and recess pattern (pattern constituted by protrusions and recesses) of a mold to the immobilization layer by imprinting process; supplying the self-organizing material to that surface of the immobilization layer on which the protrusion and recess patterned is transferred; and immobilizing the self-organizing material according to the protrusion and recess pattern of the immobilization layer by utilizing the self-organizing ability of the self-organizing material and the binding ability of the binding material contained in the immobilization layer.

According to the method, the pattern in which the material (self-organizing material) having the self-organizing ability is to be patterned, is formed in the protrusion and recess pattern of the mold, and transferred to the immobilization layer by the imprinting process, the immobilization layer containing the binding material capable of binding with the self-organizing material. The self-organizing material is supplied to the that surface of the immobilization layer on which the protrusion and recess pattern is transferred. The self-organizing material is immobilized according to the protrusion and recess pattern by interaction (such as covalent bonding, electrostatic interaction, hydrogen bonding, coordinate bonding, and hydrophobic or hydrophilic interaction) by the self-organizing ability of the self-organizing material itself, and the binding ability of the binding material.

Therefore, this method does not need radiation of x ray, electron beam, ion beam, or the like, or use of an organic solvent. Thus, this method will not cause losing the structure and the function of the self-organizing material, even though the self-organizing material is a bio material such as a nucleic acid or the like. Further, this method does not need subjecting the self-organizing material to imprinting. Thus, this method will not cause losing the structure and the function of the self-organizing material due to pressure and heat applied in imprinting, unlike the case where the self-organizing material is directly imprinted.

Because the protrusion and recess pattern of the immobilization layer is formed by imprinting, the method is not limited to a particular material of the substrate unlike the methods described in Non-Patent Citations 9 and 10. Thus, the substrate may be made of any material on the surface of which a film layer containing a binding material can be formed. Thus, the self-organizing material can be immobilized in a predetermined pattern on various substrates such as insulator substrates, semiconductor substrates, and electrically conductive substrates.

In order to attain the object, a method according to the present invention is a method of producing a self-organizing material-patterned substrate in which a self-organizing material having a self-organizing ability is patterned in a predetermined pattern on the substrate, the method including: the immobilization layer forming step including: forming, on a substrate, an immobilization layer containing a binding material having an ability of binding with the self-organizing material having a self-organizing ability; and patterning the immobilization layer by transferring a protrusion and recess pattern of a mold to the immobilization layer by imprinting process; and the self-organizing material immobilizing step including: supplying the self-organizing material to that surface of the immobilization layer on which the protrusion and recess patterned is transferred; and immobilizing the self-organizing material according to the protrusion and recess pattern of the immobilization layer by utilizing the self-organizing ability of the self-organizing material and the binding ability of the binding material contained in the immobilization layer.

According to the method, the immobilization layer forming step and the self-organizing material immobilizing step make it possible to pattern the self-organizing material in a desired pattern according to the protrusion and recess pattern transferred to the immobilization layer by imprinting, but without directly imprinting the self-organizing material.

Therefore, as explained above for the method of patterning the self-organizing material, this method does not need radiation of x ray, electron beam, ion beam, or the like, or use of an organic solvent. Further, this method does not need subjecting the layer of the self-organizing material to imprinting. Thus, the method can immobilize the self-organizing material in a predetermined pattern on the substrate without losing the structure and the function of the self-organizing material. Moreover, the substrate may be made of any material on the surface of which a film layer containing a binding material can be formed. Thus, the self-organizing material can be immobilized in a predetermined pattern on various substrates such as insulator substrates, semiconductor substrates, and electrically conductive substrates.

In order to attain the object, a self-organizing material-patterned substrate according to the present invention is a self-organizing material-patterned substrate on which a self-organizing material having a self-organizing ability is patterned in a predetermined pattern, the self-organizing material-patterned substrate including: a substrate; and an immobilization layer and a self-organizing material-patterned layer on the substrate, the immobilization layer containing a binding material having an ability of binding with the self organizing material and having a protrusion and recess patterned on its surface, and the self-organizing material-patterned layer being formed by immobilizing the self-organizing material in a recess portion of the immobilization layer by the self-organizing ability of the self-organizing material itself and the binding ability of the binding material.

In this configuration, the self-organizing material-patterned substrate includes the immobilization layer and the self-organizing material-patterned layer on the substrate, the immobilization layer containing the binding material having the ability of binding with the self organizing material and having the protrusion and recess patterned on its surface, and the self-organizing material-patterned layer being formed by immobilizing the self-organizing material in a recess portion of the immobilization layer by the self-organizing ability of the self-organizing material itself and the binding ability of the binding material. In this configuration, the self-organizing material can be patterned in a predetermined pattern by the method according to the present invention of patterning the self-organizing material, or the method according to the present invention of producing the self-organizing material-patterned substrate.

The self-organizing material may be a nucleic acid in the method according to the present invention of patterning the self-organizing material, the method according to the present invention of producing the self-organizing material-patterned substrate, or the self-organizing material-patterned substrate according to the present invention. The present invention makes it possible to pattern the nucleic acid such as DAN in a predetermined pattern without losing the structure and function of the nucleic acid. As a result, it becomes possible to crease nano bio device in which the nucleic acid is used as a functional material.

Moreover, the binding material may be poly-L-lysine or aminosilane in the method according to the present invention of patterning the self-organizing material, the method according to the present invention of producing the self-organizing material-patterned substrate, or the self-organizing material-patterned substrate according to the present invention. Poly-L-lysine can immobilize DNA, which is a nucleic acid, while aminosilane can immobilize proteins, cells, tissue sections, etc. apart from DNA.

A photomask according to the present invention includes the self-organizing material-patterned substrate according to the present invention.

With this configuration in which the photomask includes the self-organizing material-patterned substrate, it becomes possible to use, as a photomask, a transparent substrate soluble in an organic solvent, unlike photomasks such as chrome mask, made of inorganic or metal material. This makes it possible to perform a photomask-integrated lithography process. It is expected that this will provide a simpler process that results in improvements in yield and the like. Moreover, it becomes possible to decompose the substrate and DNA by chemical treatment or heat treatment. This makes it possible to remove the substrate and DNA at once. Therefore, the photomask of the present invention can be used as a photomask decomposable to remove, which has not been provided conventionally. Furthermore, the approximately-2 nm diameter of the DNA chain makes it possible to provide a 2 nm mask pattern, which cannot be attained theoretically by the lithography technique at present.

Moreover, the self-organizing material-patterned substrate according to the present invention may be configured such that a nucleic acid as the self-organizing material is modified with metal. In this configuration, the metal is a typical metal or a transition metal. The transition metal preferably includes at least one of gold, silver, platinum, palladium, iridium, rhodium, osmium, and ruthenium.

It is known that the nucleic acid can be modified with metal. By modifying the nucleic acid with metal, it is possible to pattern the metal according to the pattern of the nucleic acid on the substrate. Thus, it is possible to construct a nano-scale circuit by pattering the metal film without using the conventional lithography technique.

Moreover, the self-organizing material-patterned substrate according to the present invention may be arranged such that a pigment is inserted in a nucleic acid as the self-organizing material.

The base portion of the nucleic acid allows insertion (intercalation) thereto by pi stacking, while the phosphate portion of the nucleic acid can bind with various cationic substances. The nucleic acid to which the pigment is inserted can be electrically conductive by exiting the pigment by light radiation. Thus, the nucleic acid can be use as a functional electrically conductive material. The pigment may be acridine orange.

For a fuller understanding of the nature and advantages of the invention, reference should be made to the ensuing detailed description taken in conjunction with the accompanying drawings.

BEST MODE FOR CARRYING OUT THE INVENTION

Figure 1:
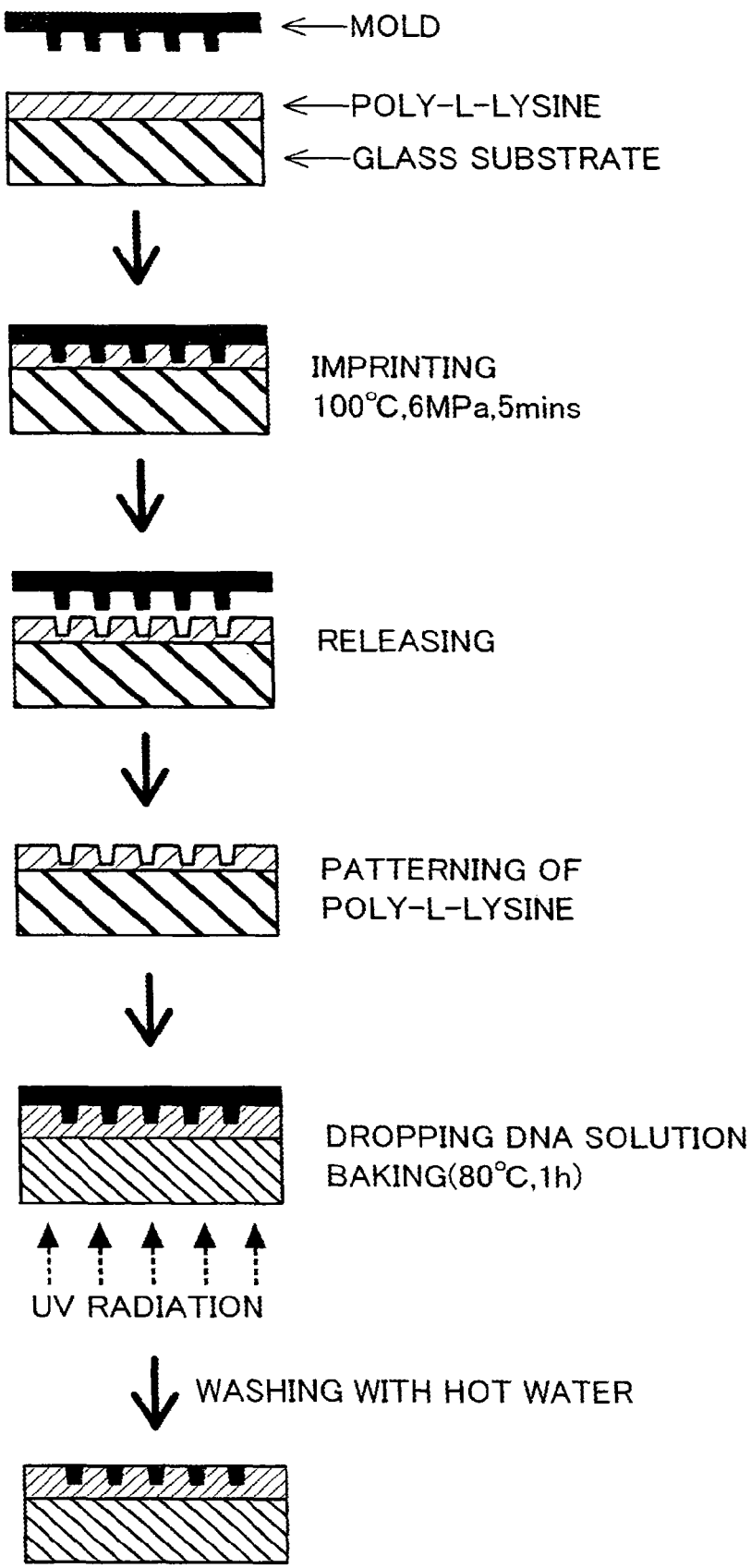
FIG. 1 is a view illustrating steps of a method for producing a self-organizing material-patterned substrate according to the present invention.
Figure 2:
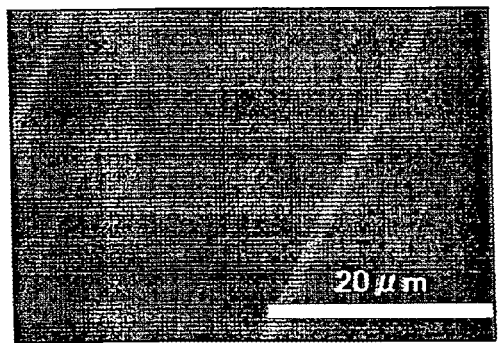
FIG. 2(a) is a view illustrating a result of observation of a pattern of DNA immobilized on a substrate according to Example. The DNA was observed using a fluorescence microscope, after being stained with a fluorochrome dropped on self-organizing material-patterned substrate. The DNA was immobilized in lines parallel with each other.
FIG. 2(b) is a view illustrating a result of observation of a pattern of DNA immobilized on a substrate according to Example. The DNA was observed using a fluorescence microscope, after being stained with a fluorochrome dropped on self-organizing material-patterned substrate. The DNA was immobilized in square lattices.
FIG. 2(c) is a view illustrating a result of observation of a pattern of DNA immobilized on a substrate according to Example. The DNA was observed using a fluorescence microscope, after being stained with a fluorochrome dropped on self-organizing material-patterned substrate. The DNA was immobilized in oblong lattices.
FIG. 2(d) is a view illustrating a result of observation of a pattern of DNA immobilized on a substrate according to Example. The DNA was observed using a fluorescence microscope, after being stained with a fluorochrome dropped on self-organizing material-patterned substrate. The DNA was immobilized in square lattices and oblong shapes within the square lattices.
Figure 2:
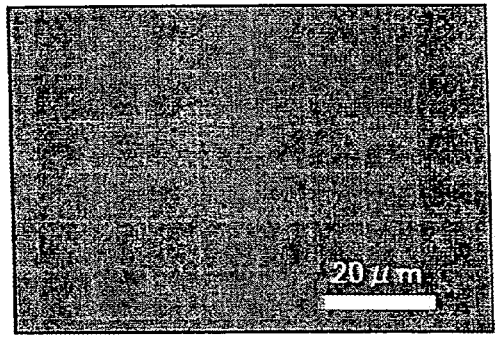
Figure 2:
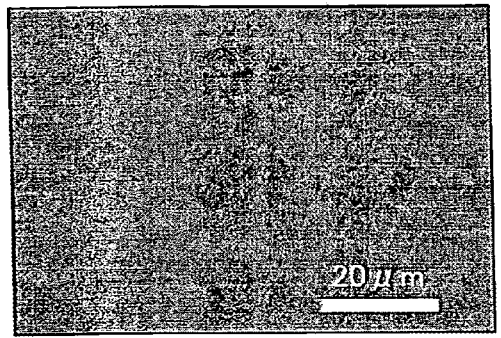
Figure 2:
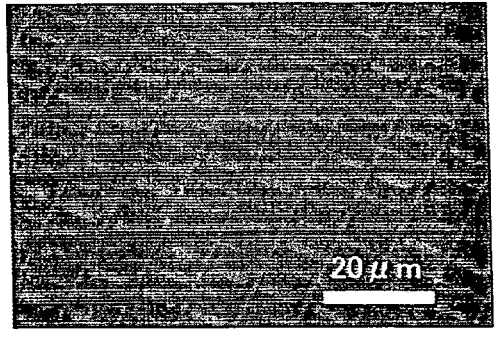
Figure 3:
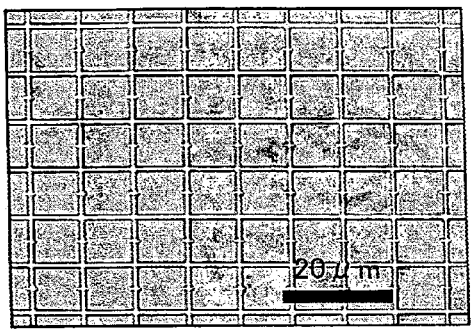
FIG. 3(a) is a view illustrating a mold made of silicon dioxide for a square lattice pattern in which DNA was to be immobilized.
FIG. 3(b) is a view illustrating a substrate on which was imprinted with the mold illustrated in FIG. 3(a) and DNA was immobilized.
FIG. 3(c) is a view illustrating a mold made of silicon dioxide for a pattern of square lattices including oblong shapes, in which DNA was to be immobilized.
FIG. 3(d) is a view illustrating a substrate on which was imprinted with the mold illustrated in FIG. 3(c) and DNA was immobilized.
Figure 3:
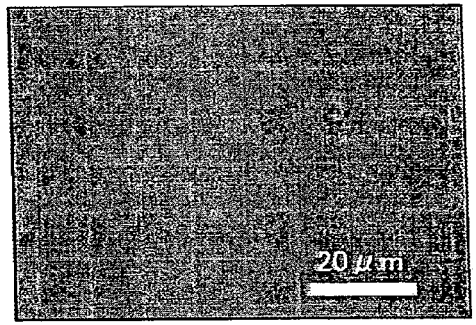
Figure 3:
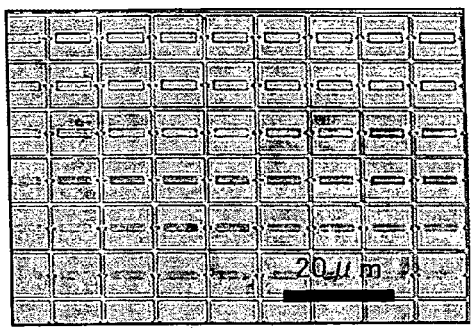
Figure 3:
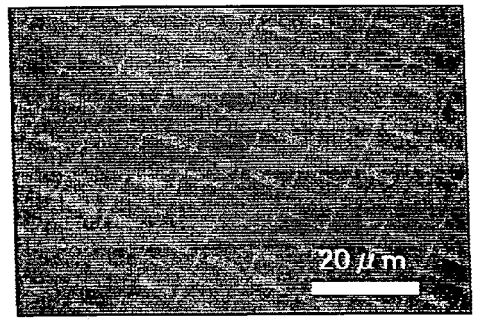
Figure 4:
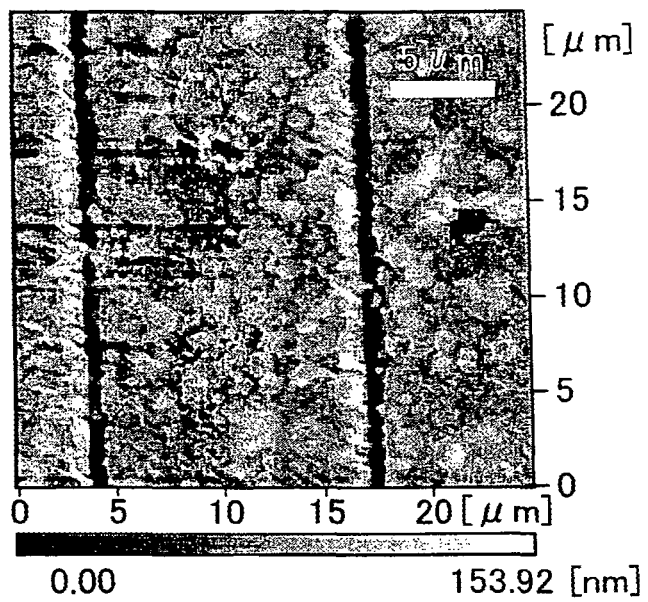
FIG. 4(a) is a view illustrating the result of atomic force microscopic observation of a DNA pattern on a self-organizing material-patterned substrate before being modified with gold colloid.
FIG. 4(b) is a view illustrating the result of atomic force microscopic observation of a DNA pattern on a self-organizing material-patterned substrate modified with gold colloid.
Figure 4:
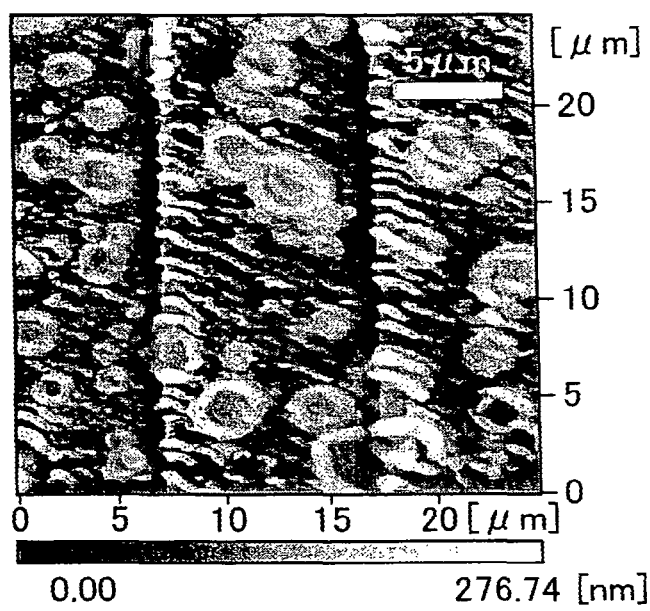

One embodiment of the present invention is described below, referring to FIGS. 1 to 7. It should be noted that the present invention is not limited to the embodiment.

A method of the present invention for producing a self-organizing material-patterned substrate utilizes a method of the present invention for patterning the self-organizing material, and includes, at least, the immobilization layer forming step of forming an immobilization layer and the self-organizing material immobilizing step of immobilizing the self-organizing material. Each of the steps is described below.

The immobilization layer forming step is a step for forming an immobilization layer on the substrate. On the immobilization layer the self-organizing material will be immobilized. In this step, the immobilization layer, containing a binding material capable of binding with the self-organizing material, is formed on the substrate by coating, immersing, or the like method. The self-organizing material can be surely immobilized on the substrate by the immobilization layer formed on the substrate, the immobilization layer containing the binding material capable of binding with the self-organizing material having a self-organizing ability (an ability of forming a structure by spontaneous gathering of many molecules).

The binding material is not particularly limited, provided that is can bind with the self-organizing material having the self-organizing ability. However, it is preferable that the binding material contain poly-L-lysine or aminosilane.

It is known that Poly-L-lysine has an ability of binding with DNA, which is a nucleic acid (B, Xu., S. Wiehle., J A. Roth., and R J. Cristiano., Gene Therapy (5), 1235-1243, 1998). Thus, Poly-L-lysine can be preferably especially for immobilizing DNA from among self-organizing materials. There is no particular limitation in terms of polymerization degree of Poly-L-lysine. The binding between DNA and Poly-L-lysine is due to static electrical interaction between negative charges on phosphate groups of DNA and positive charges on protonated amino groups of Poly-L-lysine. Therefore, it is preferable that the amino groups of Poly-L-lysine are provided with appropriate intervals. For this reason, it is preferable that the polymerization degree of Poly-L-lysine is approximately 20,000. However, the present invention is not limited to this polymerization degree of Poly-L-lysine.

Moreover, aminosilane is a material widely used for immobilizing a biomaterial, and can immobilize materials having a self-organizing ability, such as proteins, cells, tissue section, and the like, apart from DNA. Thus, the use of aminosilane in the immobilization layer makes it possible to immobilize the materials having the self-organizing ability on the substrate in a desired pattern. For example, it is possible to artificially pattern nerve cells to form a biocommunication circuit.

A thin film layer, which contains the binding material and becomes the immobilization layer, may be formed by any method, encompassing methods conventionally known. For example, spin-coating method, dipping method, and the like can be employed preferably. Moreover, the substrate is not particularly limited in terms of a material from which it is made, provided that the thin film layer containing the binding material can be formed on the substrate. For example, a glass substrate, an insulator substrate (such as resin substrate, silicone substrate, etc.) a semiconductor substrate, an electrically conductive substrate, and the like may be used as the substrate.

Onto the thin film layer, which contains the binding material and is the immobilization layer formed on the substrate, a protrusion and recess pattern formed on a mold is transferred by using an imprinting process. The protrusion and recess pattern formed on the substrate in advance represents a shape in which the self-organizing material is to be patterned on the substrate. Raised portions of the mold represents the shape of the self-organizing material obtained finally.

The mold to be used in this step is not particularly limited in terms of a material from which it is made. It is, however, preferable to make the mold from silicon or silicon dioxide Because micro fabrication techniques such as lithography are well established for these materials. Processing of the mold can be performed in a conventionally known method. For example, the mold may be formed by applying a resist (an organic film photosensitive to ultra violet ray) on a thermally-oxidized silicon film, and patterning the resist with an electron beam directly radiated thereon, and then dry-etching the thermally-oxidized silicon film masked with the patterned resist.

A conventionally known imprinting method is used to transfer the protrusion and recess pattern of the mold to the layer containing the binding material. For example, a thermocycle nanoimprinting lithography, optical nanoimprinting lithography, or the like may be employed.

Temperature, pressure, and periodical conditions in the imprinting of the protrusion and recess pattern of the mold to the immobilized layer may be decided considering (i) reduction in throughput due to time taken by heating and cooling the immobilization layer, (ii) a dimensional change in the immobilization layer due to temperature difference, (iii) accuracy of transferred pattern, (iv) deterioration in alignment due to thermal expansion, (v) and the like.

The mold is separated from the substrate after the transfer, thereby completing the immobilization layer patterned with the protrusion and recess pattern. For example, the mold is separated from the substrate after the immobilized layered is hardened by lowering the temperature of the immobilized layer in the case of the thermocycle nanoimprinting lithography. Again for example, in case of the optical nanoimprinting lithography, the mold is separated from the substrate after the immobilization layer is hardened by ultra violet ray radiated thereon.

The self-organizing material immobilizing step is a step including supplying the self-organizing material on that surface of the immobilization layer formed in the immobilization layer forming step, on which the protrusion and recess pattern is transferred, and immobilizing the self-organizing material according to the protrusion and recess pattern of the immobilization layer by utilizing the self-organizing ability of the self-organizing material itself and the binding ability of the binding material contained in the immobilization layer.

The self-organizing material may be typically a nucleic acid such as DNA, RNA, or the like, but also may be a biomolecule such as a protein, lipid, sugar, or the like, cells, a tissue section, or the like. When supplied onto the immobilization layer, the self-organizing material is preferably in a form of an aqueous solution, but is not limited to such a form, provided that the recess portion of the surface of the immobilization layer on which the protrusion and recess pattern is formed can be filled with the self-organizing material without denaturing the self-organizing material.

There is no particular limitation as to means for immobilizing, in accordance with the protrusion and recess pattern transferred to the immobilized layer, the self-organizing material supplied in the recess portion of the immobilization layer. The immobilizing may be achieved by ionic bonding, covalent bonding, hydrogen bonding, van deer Waals bonding, coordinate bonding, other like between the molecules of the self organizing material and immobilization layer. For example, in case where DNA is used as the self-organizing material and poly-L-lysine or aminosilane is used for the immobilization layer, DNA is immobilized by ionic bonding with poly-L-lysine or aminosilane, because DNA is negatively charged and poly-L-lysine and aminosilane are positively charged.

As described above, the method according to the present invention for producing the self-organizing material-patterned substrate is arranged such that (i) the immobilization layer containing the binding material capable of binding with the self-organizing material having the self-organizing ability is formed on the substrate in the immobilization layer forming step, (ii) a certain protrusion and recess pattern formed on the mold is transferred to the immobilization layer by the step of imprinting, and then (iii) the self-organizing material is supplied to the recess portion of the immobilization layer (on which the protrusion and recess pattern is formed) and the self-organizing material is immobilized according to the protrusion and recess pattern transferred on the immobilization layer in the self-organizing material immobilizing step.

By this, it is possible to obtain a self-organizing material-patterned substrate wherein an immobilization layer and a self-organizing material patterned layer are provided on a substrate, the immobilization layer containing a binding material capable of binding with the self-organizing material and having a surface on which a protrusion and recess pattern is formed, the self-organizing material patterned layer being such that the self-organizing material is immobilized in a recess portion of the protrusion and recess pattern of the immobilization layer by the self-organizing ability of the self-organizing material itself and the binding ability of the binding material, the self-organizing material being patterned in a predetermined pattern.

This method does not utilizes an organic solvent nor radiation of x-ray, electron beam, ion beam, or the like. Thus, this method does not damage the structure and function of the self-organizing material even if the self-organizing material is a biomaterial such as nucleic acid or the like. Furthermore, this method does not need of subjecting the self-organizing material itself to imprinting. Thus, this method will not cause a damage to the structure and function of the self-organizing material by the pressure, heat or light for the imprinting, unlike the case where the self-organizing material itself is directly imprinted.

Moreover, the protrusion and recess pattern of the immobilization layer is formed by imprinting. Thus, the material of the substrate is not limited as in the methods described in Non-Patent Citations 9 and 10, and can be any material provided that a film layer containing the binding material can be formed on the surface of the substrate. The method of the present invention allows using various types of substrates such as an insulator substrate, a semiconductor substrate, and a conductor substrate, in order to immobilize the self-organizing material in a desired pattern thereon.

The use of the self-organizing material-patterned substrate of the present invention allows nano-patterning of metal, for example. That is, the nucleic acid such as DNA or the like, which is the self-organizing material, can be modified with various metals. Therefore, it becomes possible to pattern metal by a soft process instead of the conventional lithography, by using, as a template, the nucleic acid patterned in a predetermined pattern without losing it structure and function as such, and immobilized on the substrate.

This method makes it possible to construct a nano-scale circuit in the pattern of DNA or RNA immobilized on the substrate. This method also makes it possible to provide the substrate with conductivity due to electron tunnel. Further, this method makes it possible to create a nano-bio device in which the nucleic acid is used as a functional material.

The metal may be a typical metal or transition metal. However, it is preferable that the metal be a noble metal because it has a good electric conductivity and is chemically stable.

The substrate may be modified with the metal by any method encompassing conventionally known methods. For example, methods described in the followings may be employed: K. Keren, R. S. Berman, and E. Braun, Nano Lett. (4), 323, 2004, J. Richter, M. Mertig and W. Pompe, Appl. Phys. Lett. (78), 536, 2001, E. Braun, Y. Eichen, U. Sivan, Nature, (391), 775, 1998, R. Seidel, M. Mertig and W. Pompe, Surf. Interface Anal. (33), 151, 2002, S. O. Kelly, J. K. Barton, N. M. Jackson, L. D. McPherson, A. B. Potter, E. M. Spain, M. J. Allen and M. G. Hill, Langmuir. (14), 6781, 1998.

Moreover, the self-organizing material-patterned substrate of the present invention may be used as a functional electrically-conductive material. DNA and RNA are functional electrically-conductive materials that have characteristic energy levels and particular properties. Moreover, it is known that the electric properties of DNA and RNA are largely changed by doping with a certain kind of element.

Further, it is possible to intercalate a pigment in the base portion of DNA by pi stacking, and it is possible to interact the base portion of RNA with a pigment. in a DNA intercalated with a pigment or RNA interacted with a pigment, the pigment is exited by light radiation, causing an electric conductivity in the DNA chain or RNA chain.

Therefore, the self-organizing material-patterned substrate can be used as a functional electrically conductive material by intercalating a pigment in DNA immobilized thereon, or interacting, with a pigment, RNA immobilized thereon. That is, it is possible to construct a light switching material that emit light in the pattern of DNA or RNA aligned on the substrate.

There is no particular limitation as to the pigment. However, acridine orange can be preferably used because this pigment has an energy level very close to these of DNA and RNA when the pigment is excited by light. Typical examples of intercalator encompass ethidium bromide, octadecyl acridine orange, ferrocenyl naphthalenediimide, β-carboline, anthoraquinone, bisacridine viologen derivatives, Ru complexes, and the like.

Moreover, it is possible to produce a photomask by using the self-organizing material-patterned substrate. A "photomask" represents a pattern image via its mask blank (JIS Industrial Terminological Dictionary, 5th Edition, page 1954, Japanese Standards Association). Inorganic or metal materials are used to produce the photomask. A typical example of the photomask is a chrome mask.

On the other hand, in the case of the use of the self-organizing material-patterned substrate as a photomask, the use of, for example, a nucleic acid such as DNA or RNA, allows removing the photomask at once by chemical treatment with an acid, alkali or the like, or heat treatment. Therefore, the use of the self-organizing material-patterned substrate as a photomask makes it possible to perform micro fabrication with DNA or RNA immobilized in a desired pattern, and simplifies the micro fabrication by performing post-process removal of the photomask by decomposition, thereby attaining better yield or the like.

Next, described below is an example in which it was confirmed, by surface plasmon resonance (SPR), that the self-organizing material-patterned substrate according to the present invention was improved significantly in an amount of adsorbed DNA, compared with a non-imprinted substrate.

To begin with the principle in determination of the amount of adsorbed DNA by the SPR phenomenon is explained. Prepared is a substrate on one side of which a metal thin film is formed and a thin film containing the binding material (hereinafter, this thin film is just referred to as just "thin film") is formed on the metal thin film. The substrate is set such that a prism is in touch with that side of the substrate on which the metal thin film is not formed. When light enters into the prism at an angle equal to or greater than total reflection angle, light called "evanescent wave" comes out slightly. On the surface of the metal thin film, a surface wave called "surface plasmon" occurs. Surface plasmon is dependent on the refractive index of the thin film that touches the metal thin film. When light enters at an incident angle at which a wave number of the evanescent wave and a wave number of the surface plasmon are equal, the energy of the incident light is utilized to excite the surface plasmon. Thus, reflection light is reduced when the surface plasmon occurs. This phenomenon is the "SPR".

Moreover, the change in the refractive index of the thin film layer can be worked out from the extent of the reduction in the intensity of the reflection light. Therefore, intensity of the surface plasmon is dependent on the change in the refractive index of the thin film surface and on the change in dielectric constant (because the dielectric constant is equal to the square of the refractive index). As the greater amount of a substance(s) is immobilized on the thin film layer, the change in the refractive index of the thin film layer becomes larger. The refractive index is proportionally dependent on the concentration of the substance immobilized on the thin film layer. Thus, if the substance immobilized on the thin film layer is DNA, the refractive index of the thin film layer would be proportionally dependent on the concentration of DNA.

Therefore, the intensity of the surface plasmon indicates the concentration of DNA immobilized on the thin film layer. That is, the change in the refractive index of the thin film layer is measured when light enters therein at the incident angle at which the wave number of evanescent wave and the wave number of surface plasmon are equal. According to the Fresnel's formula, the change in the refractive index can be converted into the concentration of the DNA immobilized on the thin film layer.

Figure 5:
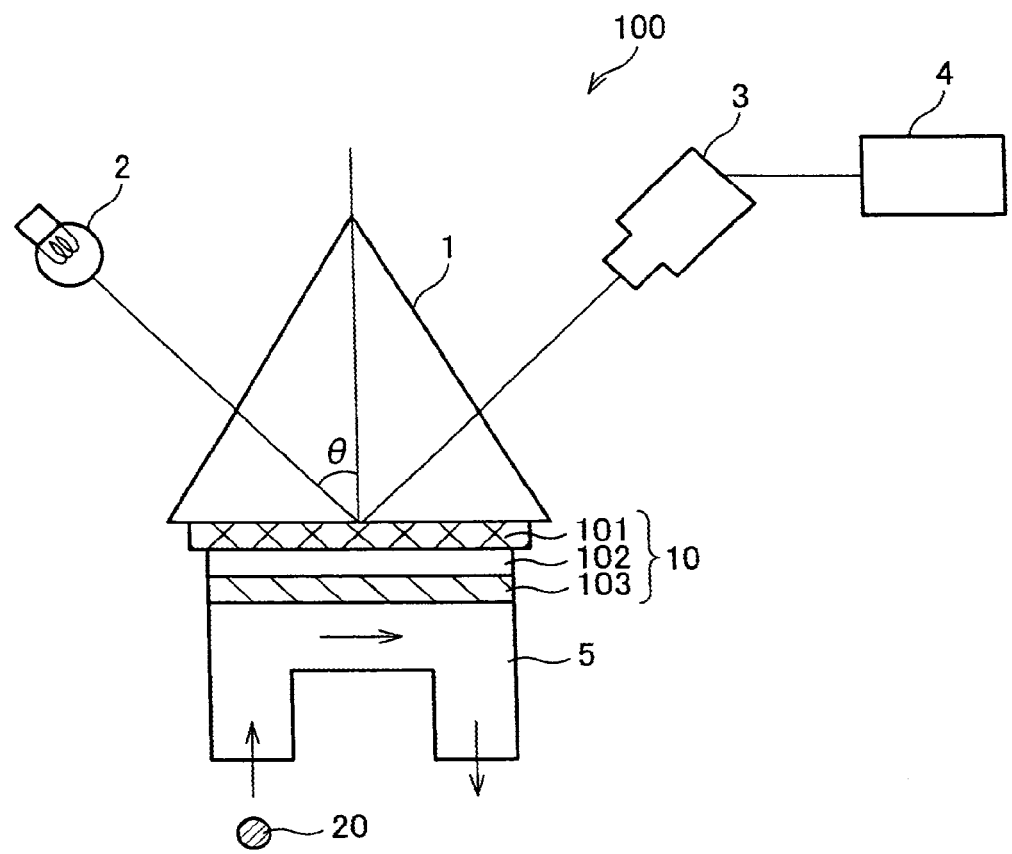
FIG. 5 is a view schematically illustrating a structure of a surface plasmon resonance apparatus.

FIG. 5 is a view schematically illustrating a structure of a surface plasmon resonance apparatus 100 for working out the change in the refractive index of the thin film layer by utilizing the surface plasmon resonance (SPR) phenomenon.

The surface plasmon resonance apparatus 100 includes a prism 1, a light source 2, a camera 3, a computer 4, and a flow path 5. Between the prism 1 and the flow path 5, a sample 10 will be set.

The sample 10 is prepared by forming a metal thin film 102 on one side of a substrate 101, and a thin film layer 103 containing a binding material (hereinafter, this layer is referred to as just "thin film layer 103") thereon. As illustrated in FIG. 5, the sample 10 is set between the prism 1 and the flow path 5 in such a manner that the surface of the sample 10 on which the metal thin film 102 and the thin film layer 103 are formed is in touch with the flow path 5, in order to immobilize DNA on the sample 10. Moreover, the other surface of the sample 10 on which the metal thin film 102 is not formed is in touch with the prism 1.

The substrate 101 may be made of any material mentioned above. The thin film layer 103 may be formed on the substrate 101 by the method described above. The metal thin film 102 may be formed on the substrate 101 by a conventionally known method, for example, by vacuum deposition method. The vacuum deposition method encompasses resistance heating, electron gun deposition method, sputtering method, and the like.

As the sample 10, a sample 10a and a sample 10b are used. The sample 10a is a sample whose thin film layer 103 is imprinted by a mold, and the sample 10b is a non-imprinted sample. The imprinting may be carried out by the method described above.

The prism 1 enters and reflects light that is supplied from the light source 2. The prism 1 may a conventionally known prism.

The light source 2 radiates light on the prism 1 and is positioned such that the light therefrom enters the prism 1 at an angle equal to or greater than the total reflection angle. The light source 2 may be any type of light source, and may be a light-emitting diode (LED), a laser diode (LD), a fluorescent lamp, a halogen lamp, or the like.

The camera 3 receives the light reflected from the prism 1 and picks up an image thereof. The camera 3 is not limited to a particular kind, and may be a line sensor camera, an area sensor camera, a CCD camera, an NIR camera, or the like.

Using the Fresnel's formula, the computer 4 calculates out the refractive index of the thin film layer 103 based on the image of the reflection light picked up by the camera 3. The computer 4 works out the amount (concentration) of DNA immobilized on the thin film layer 103 from the change in the refractive index (because the refractive index is proportionally dependent on the concentration of DNA). The Fresnel's formula is an equation for finding reflectance, which varies depending on incident angle of light and refractive index of a substance. Thus, the reflectance can be worked out from the incident angle of light and refractive index of the substance.

As described above, SPR occurs when the light enters at an incident angle at which the wave number of the evanescent wave and the wave number of the surface plasmon are equal. The SPR reduces the intensity of refection light reflected from the prism 1. The computer 4 calculates out a surface plasmon resonance energy from the reduction in the intensity of the reflection light, thereby working out dielectric constant of the thin film layer 103 (this process partially utilizes the Fresnel's formula). Furthermore, the computer 4 works out the refractive index of the thin film layer 103 from the dielectric constant which is equal to the square of the refractive index of the thin film layer 103. Moreover, the computer 4 works out the amount (concentration) of DNA immobilized on the thin film layer 103, because the refractive index is proportionally dependent of the amount (concentration) of DNA immobilized on the thin film layer 103.

The flow path 5 lets a solution 20 flow therethrough at a desired rate. The solution 20 is a solution of DNA that is to be analyzed.

Next, explained is how the surface plasmon resonance apparatus 100 operates. The sample 10a or 10b is placed between the prism 1 and the flow path 5 in such a manner that the surface of the sample 10a or 10b on which the metal thin film 102 and the thin film layer 103 are formed is exposed to the flow path 5. Then, light is radiated on the prism 1 at an angle equal to or greater than total reflection angle. While the DNA solution 20 flowing through the flow path 5 at a desired rate, an image of light reflected from the prism 1 is picked up by the camera 3. The image is analyzed by the computer 4. A DNA amount immobilized on the sample 10a and A DNA amount immobilized on the sample 10b thus worked out are compared. In this way, it can be confirmed that the self-organizing material-patterned substrate of the present invention is significantly improved in the amount of adsorbed DNA compared with a non-imprinted substrate.

The present invention is not limited to the configurations described above, and may be modified in many ways within the scope of the following claims. Such modifications obtained by appropriately combining technical means disclosed in different embodiments are intended to be included within the technical scope of the following claims.

The present invention is explained in more details referring Examples and FIGS. 1 to 7. It should be noted that the present invention is not limited to these. The present invention can be altered, corrected, or modified within the scope of the present invention by one skilled in the art.

EXAMPLES

An example of the method for producing the self-organizing material-patterned substrate according to the present invention is explained below.

(1. Production of Self-Organizing Material-Patterned Substrate According to the Present Invention)

FIG. 1 illustrates the steps of the method for producing the self-organizing material-patterned substrate according to the present invention. The glass substrate used was a glass substrate (made by Matsunami Glass Ind. Ltd.; for example Product Code; SD 10011, Product Name; Poly-Lysine Coat Type) on which a poly-L-lysine film was formed on a slide glass substrate in advance.

Next, the poly-L-lysine film (hereinafter, just referred to as "PLL film") was imprinted by pressing a mold thereon at 100° C. and 6 Mpa for 5 min., using a nanoimprinting apparatus (made by OBDUCAT AB). The PLL film was hardened by lowering the temperature down approximately to room temperatures, while keeping the applied pressure (6 Mpa). After the hardening of the PLL film, the mold was separated from the substrate, whereby a protrusion and recess pattern for DNA was completed on the PLL film.

The mold was a Si wafer on which a $SiO_2$ thermally-oxidized film was formed on Si. The $SiO_2$ thermally-oxidized film was patterned by lithography by using a stepper.

Then, approximately 100 µl of a DNA aqueous solution (1 µg/ml) was dropped all over a PLL-coated glass surface thus imprinted, the DNA aqueous solution containing salmon sperm DNA powder (made by Nippon Chemical Feed Co., Ltd.), and a buffer aqueous solution containing 0.3 mol/l of sodium chloride, and 0.03 mol/l sodium citrate. After that, the substrate was heated (baking) at 80° C. for 1 hour by a hot plate, in order to evaporate moisture therefrom, thereby facilitating immobilizing of DNA and the PLL film. Furthermore, ultra violet ray of 254 nm was radiated thereon for 5 min by a ultra violet radiator, thereby facilitating immobilization of DNA and PLL film. Next, the substrate was washed with water, and then with hot water (approximately 80° C.), thereby removing redundant DNA from the surface of the substrate. In this way, a self-organizing material-patterned substrate was completed.

(2. Observation of Pattern of DNA Immobilized on Substrate)

FIGS. 2(a) to 2(d) illustrates results of observation of patterns of DNA immobilized on self-organizing material-patterned substrates as described above. The DNA was observed using a fluorescence microscope (made by Olympus Corp, magnification ×100) after being stained with a fluorochrome dropped on the respective self-organizing material-patterned substrates. In FIGS. 2(a) to 2(d), the white lines are DNA immobilized on the substrates. In FIG. 2(a), DNA was immobilized in straight lines parallel to each other. In FIG. 2(b), DNA was immobilized in square lattices. In FIG. 2(c), DNA was immobilized in oblong lattices. In FIG. 2(d), DNA was immobilized in square lattices and oblong shapes within the square lattices.

FIGS. 3(a) to 3(d) illustrate (i) molds that was made of silica dioxide and on which the pattern in which DNA was to be immobilized was structured, and (ii) results of observation of the pattern on the substrate after imprinting of the mold and the immobilization of DNA. FIG. 3(a) illustrates the mode for square lattices, and FIG. 3(b) illustrates a substrate on which the mold illustrated in FIG. 3(a) was imprinted and DNA was immobilized. FIG. 3(c) illustrates a mold for square lattices in which oblong shapes are included. FIG. 3(d) illustrates a substrate on which the mold illustrated in FIG. 3(c) was imprinted and DNA was immobilized.

(4. Modification of DNA with Gold Colloid)

By using the DNA pattern of the self-organizing material-patterned substrate thus obtained, DNA was modified with gold colloid thereby aligning gold colloid on the DNA surface. To begin with, a commercially-available gold colloidal solution (made by Tanaka Kikinzoku Kogyo: Particle diameter; 40 nm, concentration; 0.006 wt %) was centrifuged (Conditions: 15000 rpm for one hour). After precipitates were removed, the solution was centrifuged again (Conditions: 15000 rpm for one hour). The gold colloid thus concentrated was diluted with water by the order of ten times, thereby obtaining a gold colloid solution. Into the gold colloid solution, the self-organizing material-patterned substrate with DNA patterning was immersed for approximately 2 hours, thereby modifying DNA with gold colloid. After immersing, the substrate was removed from the gold colloid solution, and excess moisture on the substrate was removed by using a blower.

FIG. 4(a) illustrates the result of observation of the substrate before modification with the gold colloid, while FIG. 4(b) illustrates the result of observation of the substrate modified with the gold colloid. These observations were carried out with an atom force microscope (made by Seiko Instruments Inc.). As illustrated in FIG. 4(b), the gold colloid was aligned according to the DNA pattern immobilized on the substrate illustrated in FIG. 4(a). The scales "0.00 to 153.92 nm" and "0.00 to 276.74 nm" indicate height corresponding to color thickness of the horizontal bars shown above the numerical values.

(5. Confirmation of Effect of DNA Immobilization by Using SPR Phenomenon)

A substrate (made by Biacore, Product Name: Sensor Chip Au) was supplied, on which a gold thin film 102 was formed on one side of a glass substrate 101. That side of the substrate on which the gold thin film 102 was formed was immersed with a 1% poly-L-lysine (PLL) aqueous solution for 1 day. The substrate then taken out from the PLL aqueous solution was heated at 100° C. for 1 hour by using a hot plate thereby forming a thin film layer 103 on that side of the substrate on which the gold thin film 102 was formed, the thin film layer 103 containing PLL as a binding material. As a result, a sample 10 was obtained.

Next, imprinting was carried out by using a nanoimprinting apparatus (made by OBDUCAT AB), by pressing a mold against that side of the substrate 10 on which the thin film layer 103 was formed. The mold was pressed on that side of the substrate 10 at 6 Mpa for 5 min under a temperature of 100° C. While keeping the pressure (6 Mpa), the temperature was cooled down to room temperatures thereby hardening the thin film layer 103. After the thin film layer 103 was hardened, the mold was removed from the sample, thereby completing protrusion and recess pattern of DNA on the thin film layer 103.

The mold was a Si wafer on which a SiO$_2$ thermally-oxidized film is formed on Si. The SiO$_2$ thermally-oxidized film was patterned by lithography using a stepper. As the sample 10, an imprinted sample 10a, and a non-imprinted sample 10b as a control were prepared for the analysis.

Next, the sample 10 was set in the surface plasmon resonance apparatus 100 (Biacore, Product Name; Biacore 3000). The sample 10 was so set that the side on which the metal thin film 102 and the thin film layer 103 were formed was in touch with a flow path 5, and the other side was in touch with a prism 1. Next, a buffer aqueous solution (hereinafter, referred to as 2×SSC) was introduced in the flow path 5, the buffer aqueous solution containing 0.3 mol/l sodium chloride+0.03 mol/l sodium citrate. After the SPR measurement became stable and constant, a DNA solution 20 was introduced in the flow path 5 at a rate of 10 μl/min instead of the buffer aqueous solution, the DNA solution 20 containing 2×SSC+1 μg/μl D N A and having a liquid temperature of 20° C. At 500 seconds since the beginning of the introduction of 2×SSC, the 2×SSC was again introduced instead of DNA solution 20.

Figure 6:
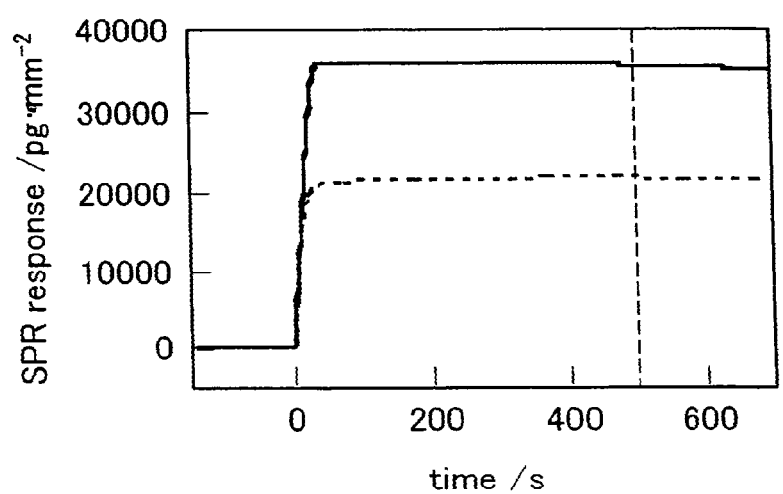
FIG. 6 is a graph illustrating the result of measurements of amounts of adsorbed DNA in imprinted and non-imprinted samples in which a gold thin film and a thin film layer containing PLL were formed on a glass substrate.

FIG. 6 shows the results. The graph of FIG. 6 shows real-time measurements displayed on a monitor since the introduction of the 2×SSC into the flow path 5. When DNA concentration was measured, the DNA concentration calculated out from intensity of reflection light on real time was displayed on the monitor. The horizontal axis indicates time (second) from the introduction of the 2×SSC, while the vertical axis indicates amount (pg) of adsorbed DNA per 1 mm$^2$ on the substrate. Moreover, the solid line shows the amount of immobilized DNA on the imprinted sample 10a over time, and the dotted line shows the amount of immobilized DNA on the non-imprinted sample 10b over time.

DNA could be immobilized on the PLL on the non-imprinted sample 10b, the amount of immobilize DNA was increased in the imprinted sample 10a by about 1.8 times as illustrated in FIG. 6.

PLL has a structure as represented by General Formula:

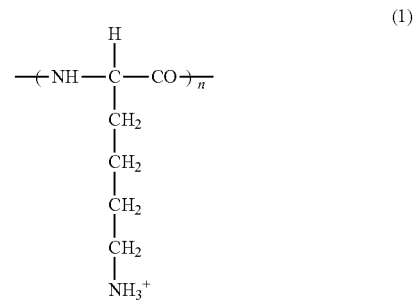

(1)

Figure 7:
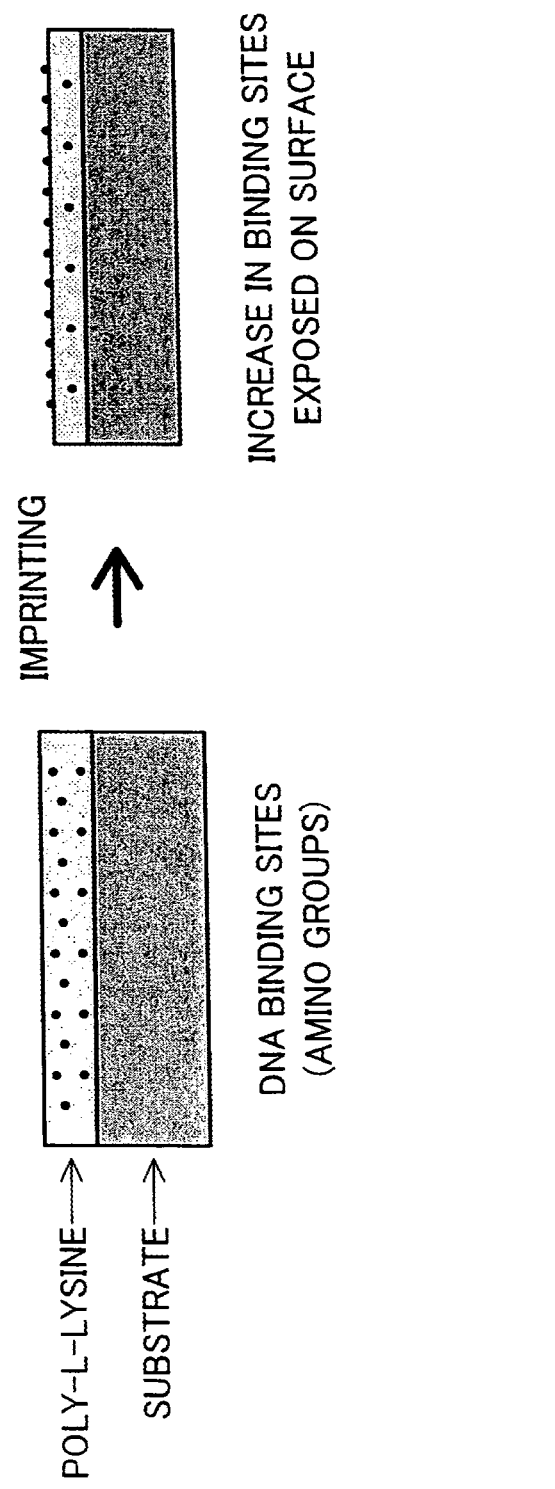
FIG. 7 is a view schematically illustrating that an amount of amino groups exposed on a surface is increased by imprinting a sample in which a thin film layer containing PLL is formed.

DNA introduced to the surface plasmon resonance apparatus 100 is bound with the amino group at the end of PLL. It is deduced that the imprinting on the sample having the thin film layer 103 thereon increases the amount of the amino groups exposed on the surface as illustrated in FIG. 7, thereby increasing the amount of immobilized DNA.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICATION

As described above, the present invention immobilizes a self-organizing material on a substrate by utilizing a self-organizing ability of the self-organizing material without imprinting the self-organizing material itself. Thus, the present invention makes it possible to immobilize the self-organizing material in a predetermined pattern easily without damaging the structure and function of the self-organizing material. Therefore, the present invention is applicable to a nano-scale circuit construction, functional electrically conductive materials, photomasks, etc.

As described above, a method according to the present invention for patterning the self-organizing material includes: forming, on a substrate, an immobilization layer containing a binding material having an ability of binding with the self-organizing material having a self-organizing ability; patterning the immobilization layer by transferring a protrusion and recess pattern of a mold to the immobilization layer by imprinting process; supplying the self-organizing material to that surface of the immobilization layer on which the protrusion and recess patterned is transferred; and immobilizing the self-organizing material according to the protrusion and recess pattern of the immobilization layer by utilizing the self-organizing ability of the self-organizing material and the binding ability of the binding material contained in the immobilization layer.

Moreover, as described above, a method according to the present invention for producing a self-organizing material-patterned substrate is a method of producing a self-organizing material-patterned substrate in which a self-organizing material having a self-organizing ability is patterned in a predetermined pattern on the substrate. The method includes: the immobilization layer forming step including: forming, on a substrate, an immobilization layer containing a binding material having an ability of binding with the self-organizing material having a self-organizing ability; and patterning the immobilization layer by transferring a protrusion and recess pattern of a mold to the immobilization layer by imprinting process; and the self-organizing material immobilizing step including: supplying the self-organizing material to that surface of the immobilization layer on which the protrusion and recess patterned is transferred; and immobilizing the self-organizing material according to the protrusion and recess pattern of the immobilization layer by utilizing the self-organizing ability of the self-organizing material and the binding ability of the binding material contained in the immobilization layer.

As described above, a self-organizing material-patterned substrate according to the present invention is a substrate on which a self-organizing material having a self-organizing ability is patterned in a predetermined pattern. The self-organizing material-patterned substrate includes a substrate, and an immobilization layer and a self-organizing material-patterned layer on the substrate, the immobilization layer containing a binding material having an ability of binding with the self organizing material and having a protrusion and recess patterned on its surface, and the self-organizing material-patterned layer being formed by immobilizing the self-organizing material in a recess portion of the immobilization layer by the self-organizing ability of the self-organizing material itself and the binding ability of the binding material.

Therefore, this method does not need radiation of x ray, electron beam, ion beam, or the like, or use of an organic solvent. Further, this method does not need subjecting the layer of the self-organizing material to imprinting. Thus, the method can immobilize the self-organizing material in a predetermined pattern on the substrate without losing the structure and the function of the self-organizing material. For example, in case where the self-organizing material is a nucleic acid such as DNA, this method makes it possible to create a nano-scale bio device in which the nucleic acid is used as a functional material.

The invention claimed is:

1. A method for performing micro fabrication, comprising:
    forming, on a substrate soluble in an organic solvent,
    an immobilization layer containing a binding material having an ability of binding with a self-organizing material having a self-organizing ability;
    transferring a protrusion and recess pattern of a mold to the immobilization layer by thermocycle nanoimprinting lithography or optical nanoimprinting lithography;
    supplying the self-organizing material to a surface of the immobilization layer on which the protrusion and recess pattern has been transferred, and
    immobilizing the self-organizing material in a recess portion of the protrusion and recess pattern of the immobilization layer, so as to obtain a self-organizing material-patterned substrate soluble in an organic solvent; and
    performing, by radiating light, reduced projection of a pattern of the self-organizing material-patterned substrate used as a photomask on a photoresist applied on a silicon substrate, and transferring or reprinting the pattern of the photomask on the photoresist, so as to perform micro fabrication,
    the self-organizing material being a nucleic acid, and
    the immobilization layer, to which the protrusion and recess pattern of the mold has been transferred, containing the binding material at a bottom surface and a side surface of the recess portion formed by the thermocycle nanoimprinting lithography or the optical nanoimprinting lithography.

2. The method as set forth in claim 1, wherein the binding material is poly-L-lysine.

3. The method as set forth in claim 1, wherein the binding material is aminosilane.

* * * * *